United States Patent [19]

Zuech

[11] 3,940,346

[45] Feb. 24, 1976

[54] SUPPORTED MOLYBDENUM OR TUNGSTEN OXIDES TREATED WITH ORGANOALUMINUM COMPOUNDS AS CATALYSTS

[75] Inventor: Ernest A. Zuech, Bartlesville, Okla.

[73] Assignee: Phillips Petroleum Company, Bartlesville, Okla.

[22] Filed: Apr. 14, 1969

[21] Appl. No.: 816,052

[52] U.S. Cl.............................. 252/430; 260/683 D
[51] Int. Cl.$^2$......................................... B01J 31/14
[58] Field of Search........................... 252/430, 428

[56] References Cited
UNITED STATES PATENTS

| | | | |
|---|---|---|---|
| 2,887,471 | 5/1959 | Shearer et al.................. | 252/430 X |
| 2,963,447 | 12/1960 | Peters et al..................... | 252/430 |
| 3,113,115 | 12/1963 | Ziegler et al................... | 252/430 |
| 3,490,745 | 1/1970 | Chappell et al................. | 252/430 |
| 3,526,601 | 9/1970 | Fotis et al....................... | 252/430 |
| 3,536,632 | 10/1970 | Kroll................................ | 252/430 |

FOREIGN PATENTS OR APPLICATIONS 714,538  7/1965  Canada

*Primary Examiner*—Patrick P. Garvin

[57] ABSTRACT

Catalysts active for the olefin reaction, including olefin disproportionation are provided comprising molybdenum or tungsten oxides associated with a suitable support material which has been subjected to treatment at high temperature in combination with organoaluminum compounds. The supported molybdenum or tungsten oxide can optionally be contacted with nitric oxide, nitrosyl halide, and alkali or alkaline earth metal compounds prior to treatment with the organoaluminum compound.

16 Claims, No Drawings

SUPPORTED MOLYBDENUM OR TUNGSTEN OXIDES TREATED WITH ORGANOALUMINUM COMPOUNDS AS CATALYSTS

FIELD OF THE INVENTION

This invention relates to the conversion of olefinic hydrocarbons and to a catalyst for such conversion. In one aspect, the invention relates to the olefin reaction. In another aspect, it relates to the conversion of olefins to other olefins having different molecular weights. In another aspect, it relates to a novel solid multi-component catalyst for effecting the conversion of olefins in accordance with the olefin reaction.

DESCRIPTION OF THE PRIOR ART

A number of catalysts are known for the disproportionation of olefins to produce other olefins of both higher and lower molecular weight. Some of these utilize oxides of tungsten or molybdenum in association with selected support materials. Processes using these catalysts require relatively high operating temperatures. For example, an alumina-supported molybdenum oxide catalyst is operable at temperatures in the range of 66°C (150°F) to about 260°C (500°F), preferably 121°C (250°F) to 204°C (400°F). The silica-supported tungsten oxide catalyst is generally utilized at temperatures above 204°C (400°F) and excellent results are obtained at temperatures in the range of 315°C (600°F) to 482°C (900°F).

More recently, a number of catalyst systems have been found which can be used to carry out such conversions at relatively low temperatures. For example, a number of homogeneous systems have been found active within the broad temperature range of from about −30° to about 150°C. These catalysts generally comprise transition metal complexes in admixture with organoaluminum compounds and are soluble in the reaction media. It is desirable to have a catalyst system which has the advantages of the low temperature operation which is characteristic of the homogeneous catalyst system but which maintains the advantages of the solid catalyst system. The solid catalysts are generally more economic in that they can be employed in fixed bed processes and can be easily separated from the reactants and products.

OBJECTS OF THE INVENTION

Accordingly, it is an object of this invention to provide for the art a catalyst system for use in accordance with the olefin reaction which has the advantages of the solid type catalyst but which is operative at lower temperatures than those generally required for a solid type catalyst. It is a further object to provide a method of converting olefins in accordance with the olefin reaction utilizing a solid catalyst which is operative at relatively low temperatures. Other objects and advantages of the invention are apparent in the specification and the claims.

SUMMARY OF THE INVENTION

The solid catalyst of the invention comprises (a) molybdenum oxide or tungsten oxide associated with a suitable support material, and (b) at least one organoaluminum compound. Further according to the invention there is provided a catalyst comprising a suitably supported molybdenum oxide or tungsten oxide material which has been treated with nitric oxide or nitrosyl halides prior to contact with, or treatment with, the organoaluminum compounds. Further according to the invention there is provided a method of converting olefins in accordance with the olefin reaction by contacting olefins with the above catalysts.

DESCRIPTION OF THE PREFERRED EMBODIMENTS

The Olefin Reaction

The term "olefin reaction", as used herein, is defined as a process for the catalytic conversion over a catalyst of a feed comprising one or more ethylenically unsaturated compounds to produce a resulting product which contains at least ten per cent by weight of product compounds, which product compounds can be visualized as resulting from at least one primary reaction, as defined below, or the combination of at least one primary reaction and at least one unsaturated bond isomerization reaction, and wherein the sum of the cmpounds contained in the resulting product consisting of hydrogen, saturated hydrocarbons, and compounds which can be visualized as formed by skeletal isomerization but which cannot be visualized as formed by one or more of the above-noted reactions, comprises less than 25 per cent by weight of the total of said resulting product. Feed components and the unsaturated bond isomers thereof are not included in the resulting product for the purpose of determining the above-noted percentages.

In the olefin reaction, as defined above, the primary reaction is a reaction which can be visualized as comprising the breaking of two existing unsaturated bonds between first and second carbon atoms and between third and fourth carbon atoms, respectively, and the formation of two new unsaturated bonds between said first and third and between said second and fourth carbon atoms. Said first and second carbon atoms and said third and fourth carbon atoms can be in the same or different molecules.

The olefin reaction is illustrated by the following reactions:

1. The disproportionation of an acyclic mono-or polyene having at least three carbon atoms into other acyclic mono- or polyenes of both higher and lower number of carbon atoms; for example, the disproportionation of propylene yields ethylene and butenes; the disproportionation of 1,5-hexadiene yields ethylene and 1,5,9-decatriene;
2. The conversion of an acyclic mono- or polyene having three or more carbon atoms and a different acyclic mono- or polyene having three or more carbon atoms to produce different acyclic olefins; for example, the conversion of propylene and isobutylene yields ethylene and isopentene;
3. The conversion of ethylene and an internal acyclic mono- or polyene having four or more carbon atoms to produce other olefins having a lower number of carbon atoms than that of the acyclic mono- or polyene; for example, the conversion of ethylene and 4-methylpentene-2 yields 3-methylbutene-1 and propylene;
4. The conversion of ethylene or an acyclic mono- or polyene having three or more carbon atoms and a cyclic mono- or cyclic polyene to produce an acyclic polyene having a higher number of carbon atoms than that of any of the starting materials; for example, the conversion of cyclooctene and 2-pentene yields 2,10-tridecadiene; the conversion of 1,5-cyclooctadiene and ethylene yields 1,5,9-decatriene;

5. The conversion of one or more cyclic mono- or cyclic polyenes to produce a cyclic polyene having a higher number of carbon atoms than any of the starting materials; for example, the conversion of cyclopentene yields 1,6-cyclodecadiene and continued reaction can give higher molecular weight materials;

6. The conversion of an acyclic polyene having at least seven carbon atoms and having at least five carbon atoms between any two double bonds to produce acyclic and cyclic mono- and polyenes having a lower number of carbon atoms than that of the feed; for example, the conversion of 1,7-octadiene yields cyclohexene and ethylene; or 7. The conversion of one or more acyclic polyenes having at least three carbon atoms between any two double bonds to produce acyclic and cyclic mono- and polyenes generally having both a higher and lower number of carbon atoms than that of the feed material; for example, the conversion of 1,4-pentadiene yields 1,4-cyclohexadiene and ethylene.

THE OLEFIN FEEDS

Olefins applicable for use in the process of the invention are nontertiary, nonconjugated acyclic mono- and polyenes having at least 3 carbon atoms per molecule including cycloalkyl, cycloalkenyl, and aryl derivatives thereof; cyclic mono- and polyenes having at least 4 carbon atoms per molecule including alkyl and aryl derivatives thereof; mixtures of the above olefins; and mixtures of ethylene and the above olefins. Many useful reactions are accomplished with such acyclic olefins having 2–30 carbon atoms per molecule and with such cyclic olefins having 4–30 carbon atoms per molecule. Non-tertiary olefins are those olefins wherein each carbon atom, which is attached to another carbon atom by means of a double bond, is also attached to at least one hydrogen atom.

It has been found that within the scope of this invention certain olefins react at a faster rate than other olefins. Also, in employing certain olefins higher conversions are obtained than with other olefins under comparable reaction conditions. For example, the contact of a symmetrical monoolefin with a catalyst of the invention to give different olefin products (i.e., the reactions exemplified under number 1 above) apparently requires some double bond migration to take place before the disproportionation reaction proceeds at a significant rate. For similar reasons, the conversion of a mixture of ethylene and a 1-olefin proceeds at a slower rate and lower conversion than the conversion of a mixture of ethylene and an internal olefin. It has also been found that branching or the presence of inert polar substituents sometimes decrease the reactivity of a double bond in the feed olefin as the branching or polar substituent approaches the double bond. Accordingly, the present invention is directed primarily to the conversion of those olefins or combination of olefins which are capable of undergoing the olefin reaction to a significant degree when contacted with the catalyst of the present invention under reaction conditions suitable for effecting the olefin reaction.

Presently preferred olefinic feed compounds are those contained in the following classes:

1. Acyclic monoolefins, including those with aryl, cycloalkyl, and cycloalkenyl substituents, having 3–20 carbon atoms per molecule with no branching closer than about the 3- position to the double bond, no quaternary carbon atoms and no aromatic substitution closer than the 4- position to the double bond, and mixtures of such unsubstituted acyclic monoolefins. Some examples of these are propylene, pentene-1, pentene-2, butene-1, butene-2, 3-methylbutene-1, hexene-2, octene-4, nonene-2, 4-methylpentene-1, decene-3, 8-ethyldecene-2, dodecene-4, vinylcyclohexane, 4-vinylcyclohexene, eicosene-1, and the like.

2. A mixture of ethylene and one or more acyclic unsubstituted internal monoolefins of (1). Some examples of such mixtures are ethylene and butene-2, ethylene and pentene-2, ethylene and hexene-3, ethylene and heptene-3, ethylene and 4-methylpentene-2, ethylene and octene-4, ethylene and dodecene-4, and the like.

3. Acyclic, nonconjugated polyenes having from 5 to about 20 carbon atoms per molecule, containing from 2 to about 4 double bonds per molecule and having no double bond with branching nearer than the 3- position to that double bond, and having at least one double bond with no quaternary carbon atoms and no aromatic substitution nearer than the 4- position to that double bond, or mixtures of such polyenes. Some examples are 1,4-pentadiene, 1,5-hexadiene, 1,7-octadiene, 2,6-decadiene, 1,5,9-dodecathriene, 4-methylheptadiene-1,6, 1,7-octadiene, 1,6-octadiene, and the like.

4. A mixture of ethylene and one or more acyclic polyenes of (3) which contain at least one internal double bond. Some examples are ethylene and 1,6-octadiene, ethylene and 1,5-decadiene, and the like.

5. Cyclopentene.

6. Cyclic and bicyclic monoolefins having 7 to 12 ring carbon atoms, including those substituted with up to 3 alkyl groups having up to about 5 carbon atoms, with no branching closer than the 3- position and with no quaternary carbon atoms closer than the 4- position to that double bond, and mixtures of such olefins including mixtures with cyclopentene. Some examples are cycloheptene, cyclooctene, 4-methylcyclooctene, 3-methyl-5-ethylcyclodecene, cyclononene, cyclododecene, norbornene, and the like.

7. A mixture of one or more of the monocyclic olefins of (6) with either ethylene or with one or more unsubstituted acyclic monoolefins of (1). Some examples of these are ethylene and cycloheptene, ethylene and cyclooctene, propylene and cyclodecene, pentene-2 and cyclooctene, ethylene and cyclododecene, and the like.

8. Cyclic and bicyclic nonconjugated polyenes having from 5 to about 12 ring carbon atoms, including those substituted with up to 3 alkyl groups having up to about 5 carbon atoms each, having at least one double bond with no branching closer than the 3-position and with no quaternary carbon atoms closer than the 4- position to that double bond, and mixtures thereof. Some examples of these are 1,5-cyclooctadiene, 1,5,9-cyclododecatriene, 1,4-cycloheptadiene, norbornadiene, and the like.

9. A mixture of one or more monocyclic polyenes of (8) with one or more acyclic 1-olefins having from 2 to about 10 carbon atoms, having no branching nearer than the 3-position and no quaternary carbon atoms nearer than the 4- position to the double bond. Some examples of these are 1,5-cyclooctadiene and ethylene, 1,5,9-cyclodecatriene and ethylene, 1,5,9-cyclododecatriene and pentene-1, and the like.

10. Polar group-substituted olefinic compounds of classes (1) through (9) containing from about 5 to about 20 carbon atoms per molecule in which the polar group, such as a halogen atom, is sufficiently removed from the active double bond (generally no nearer to the double bond than the 5- position) so as not to interfere with the reaction, and mixtures with unsubstituted members of class (1). Some examples are 5-chloropentene-1, a mixture of pentene-2 and 5-chloropentene-1, and the like.

THE CATALYSTS

The (a) components of the catalyst system of the invention, by themselves, are active for the disproportionation of olefins in accordance with the olefin reaction. However, as mentioned previously, the activity of this system is exhibited at relatively high temperatures which are generally above 150°C for optimum operation.

Suitable support materials which are combined with the oxides of molybdenum and tungsten to form the (a) component of the catalyst include alumina, silica, silica-alumina, magnesia-titania, thoria, aluminum phosphate, zirconium phosphate, titanium phosphate, calcium phosphate, magnesium phosphate, and mixtures thereof.

Preferred combinations of the above support materials with the oxides of molybdenum and tungsten promoter materials include (1) silica or thoria promoted by the oxide, or a compound convertible to an oxide by calcination, of tungsten or molybdenum; (2) alumina promoted by an oxide, or compound convertible to an oxide by calcination, of molybdenum or tungsten; and (3) one or more of the group aluminum phosphate, zirconium phosphate, calcium phosphate, magnesium phosphate, or titanium phosphate promoted by one or more of an oxide of molybdenum or tungsten, or by a compound of molybdenum or tungsten convertible to an oxide by calcination.

The combinations 9f (1), (2), or (3) can be prepared and activated by suitable methods such as, for example, impregnation, dry mixing, or coprecipitation.

When the promoter is tungsten oxide, the preferred support material is silica or silica-containing materials. The preferred support material for molybdenum oxide is alumina or alumina-containing materials. In general the (a) component of the catalyst will contain about 0.1 to about 30, preferably from about 1 to about 15, weight per cent of the molybdenum or tungsten oxide. In addition, it is sometimes desirable that this component of the catalyst system of the invention contain relatively small amounts, from about 0.005 to about 5, preferably 0.1 to 2, weight per cent, of an inorganic base material. Suitable inorganic base materials include alkali metal and alkaline earth metal hydroxides and carbonates, sodium hydroxide, potassium hydroxide, sodium carbonate and potassium carbonate being preferred.

The solid (a) component of the catalysts can be in any conventional catalytic shape or size, depending upon the type of conversion in which it is to be utilized. For example, in fixed bed catalyst systems, the solid composite can be in the form of spheres, pellets, extrudates, agglomerates, and the like. In slurry catalyst systems, the solid can be in the form of relatively small particles or in the form of a powder.

To be effective in the present catalyst system, the above-described (a) component of the catalysts is activated at elevated temperatures, generally in flowing air. The activation of the catalysts is accomplished at a temperature of from about 500° to about 1600°F for a period of several seconds to several hours. When the (a) component of the catalyst system is tungsten oxide on silica, a convenient and economical activation treatment is in the temperature range of 900° to 1200°F for a period of 15 minutes to 5 hours. When the (a) component of the catalyst system is molybdenum oxide on alumina a convenient and economical treatment is in the temperature range of 900°–1400°F for 0.5 to 20 hours or longer. In some cases the activation using an oxygen-containing gas can be followed by treatment, also at elevated temperatures, with other treating gases such as carbon monoxide, hydrogen, and the like.

The organoaluminum compounds which are applicable for use as the (b) component in the catalysts of the present invention have the formula $R_aAlX_b$ wherein R is a saturated aliphatic or aromatic hydrocarbon having up to about 20 carbon atoms, X is chlorine, bromine, iodine, or fluorine, $a$ is an integer of at least 1, $b$ can be 0, 1 or 2, and the total of $a$ and $b$ is 3. Such aluminum compounds are well known in the art and are generally commercially available.

Some examples of the organoaluminum compounds are methylaluminum dichloride, dimethylaluminum fluoride, methylaluminum sesquichloride, trimethylaluminum, ethylaluminum dichloride, ethylaluminum sesquichloride, di(2-ethylhexyl)aluminum bromide, triisobutylaluminum, phenylaluminum dichloride, di(3-methylpentyl)aluminum bromide, cyclohexylaluminum dichloride, benzylaluminum diiodide, dieicosylaluminum bromide, and the like, and mixtures thereof. The preferred (b) components are the organoaluminum halides especially those wherein the hydrocarbon portion is an alkyl radical of 1 to 5 carbon atoms. Particularly good results are obtained with ethylaluminum dichloride, diethylaluminum chloride, and mixtures such as ethylaluminum sesquichloride and methylaluminum sesquichloride.

The molar proportion of the organoaluminum (b) component to the solid (a) component to form the catalyst system of the present invention will generally be in the range of from about 0.005:1 to about 20:1, preferably from about 0.01:1 to about 10:1 mols of the (b) component per mol of the molybdenum or tungsten oxide contained in the (a) component.

It is sometimes preferred that the supported tungsten or molybdenum component, before contacting the organoaluminum compound, be treated either with nitric oxide or with nitrosyl halide. Such treatment can take place at a temperature preferably in the range of from about 0° to about 130°C, more preferably 20 to about 60°C, for a time in the range of from a few seconds up to about 24 hours, and preferably in the presence of a diluent in which the nitric oxide or nitrosyl halide is at least partially soluble. After such treatment, the diluent and excess nitric oxide or nitrosyl halide can be removed from the solid catalyst by decantation, evaporation and similar techniques. This treatment, however, should be carried out in the substantial absence of moisture, preferably in an inert atmosphere, to preserve the effects of the previous activation by calcination.

The catalyst system of the present invention is prepared simply by combining the solid (a) component with the organoaluminum (b) component under conditions of time and temperature which permit the catalytically active catalyst composition to be formed. The combination occurs very readily, and, in general, the components can be mixed at any convenient temperature, room temperature frequently being satisfactory, in the presence of a diluent in which the organoaluminum compound is at least partially soluble. Any convenient diluent such as benzene, cyclohexane, toluene, chlorobenzene, methylene chloride, ethylene chloride, and the like can be used for this purpose. Halogenated diluents are generally preferred. The mixing of these two catalyst components is carried out in the substantial absence of air or moisture, generally in an inert atmosphere. After the catalytic reaction mixture is formed, it need not be isolated but can be added directly to the olefin reaction zone as a suspension in its preparation medium. If desired, the catalyst components can be separately added, in any order, to the reaction zone either in the presence or absence of the feed olefin.

Alternatively, the catalysts of the invention can be separated from the preparation medium and the dissolved organoaluminum compound therein by decantation, and, after additional washing and/or drying if desired, can be added to the reaction zone as a solid rather than as a suspension.

According to the process of the invention, the olefin or mixture of olefins to be converted in accordance with the olefin reaction is contacted with the catalyst of the invention under conditions suitable to obtain the desired reaction with the selected feed, for example, at a temperature in the range of about 0° to about 150°C and at any convenient pressure. Preferably, the temperature is in the range of from about 15°C to about 50°C wherein good results are obtained economically. Excellent results are obtained by contacting the olefin feed material with the catalyst at room temperature. The conversion can be carried out in the presence of any inert diluent such as that used for the catalyst preparation, if desired. Diluents are not essential but are sometimes preferred and such diluents can include saturated aliphatics and aromatics such as cyclohexane, xylene, isooctane, and the like, and halogenated derivatives thereof. The time of contact will depend upon the desired degree of conversion and the catalysts and olefins utilized, but will, generally, be in the range of from about 0.1 minute to 24 hours, preferably 5–120 minutes. The proportion of catalyst composition to olefin feed in the reaction zone will generally be in the range of from about 0.001–100 millimoles of the molybdenum or tungsten oxide contained in the solid catalyst for each mole of olefin in the reaction zone.

Any conventional contacting technique can be used for the olefin conversion, and batchwise or continuous operation can be utilized. After the reaction period, the products can be separated and/or isolated by any suitable means such as by fractionation, crystallization, adsorption, and the like. Unconverted feed materials or products not in the desired molecular weight range can be recycled to the conversion zone. After separation of the products, the solid catalyst can be recycled to the reaction zone either with or without the addition of a fortifying amount of organoaluminum halide.

The catalysts and the method of the invention are illustrated by the following examples.

EXAMPLE I

Conversion of pentene-1 over $MoO_3/Al_2O_3$ in presence of methylaluminum sesquichloride (MASC)

A suspension of 9.5 g of a particulate $MoO_3/Al_2O_3$ catalyst (containing about 13 weight per cent $MoO_3$ and activated in flowing air for 5 hours at 1000°F) and 20 ml of chlorobenzene was combined with 10 o ml of pentene-1. The reaction mixture was stirred at room temperature for 2 hours. A sample was withdrawn at this time and analyzed by gas-liquid chromatography which showed that the pentene-1 was unchanged. A 0.5 ml quantity of methylaluminum sesquichloride (MASC) was then added to the reaction mixture. After another 1.5 hour the reaction mixture was hydrolyzed by the addition of water and the liquid organic phase was separated and recovered.

Analysis of the liquid phase of the reaction mixture showed the following:

| Olefins | Weight % |
|---|---|
| pentenes | 76.1 |
| hexenes | 8.0 |
| heptenes | 7.2 |
| octenes | 8.7 |

No attempt was made to analyze for the volatile ethylene, propylene, and butenes which were also present in the autoclave.

The above example illustrates that methylaluminum sesquichloride and alumina-supported molybdenum oxide provide a catalyst system for the disproportionation of olefins at room temperature.

EXAMPLE II

Conversion of pentene-1 over NOCl-treated $MoO_3$-$Al_2O_3$/MASC:

Run 1

A 6 g quantity of a particulate $MoO_3$—$Al_2O_3$ catalyst (containing about 13 weight per cent $MoO_3$, containing a small amount of KOH, and activated by heating in flowing air at 1000°F for about 5 hours) was suspended in 20 ml of chlorobenzene and treated with NOCl at 10 psig for 2 hours in a closed vessel. The chlorobenzene and other volatiles were then removed by evaporation under reduced pressure and the residual solid was washed with three 10 ml portions of chlorobenzene. The treated particulate solid catalyst was slurried with another 20 ml quantity of chlorobenzene and mixed with 1 ml of methylaluminum sesquichloride (MASC) and 10 ml of pentene-1. This mixture was stirred for 30 minutes at room temperature and then hydrolyzed by the addition of water. The organic phase was separated, recovered, and analyzed by gas-liquid chromatography. The results were as follows:

| Olefins | Weight % |
|---|---|
| pentenes | 54.8 |
| hexenes | 1.5 |
| heptenes | 2.7 |
| octenes | 41.3 |

The data in the table above show that the alumina-supported molybdena/MASC catalyst system is active for conversion of pentene-1 at room temperature and that the treatment with NOCl increases the activity and selectivity of the conversion.

Run 2

The solid catalyst, after the reaction mixture was withdrawn from the vessel, was washed with 10 ml of chlorobenzene and again used to catalyze the conversion of another 10 ml of pentene-1 which was diluted with 10 ml chlorobenzene. After one hour and 10 minutes at room temperature, this second reaction mixture was withdrawn, hydrolyzed, and analyzed, showing:

| Olefins | Weight % |
|---|---|
| pentenes | 84.1 |
| hexenes | 0.4 |
| heptenes | 0.7 |
| octenes | 14.9 |

Run 3

The solid catalyst was recovered and once again used for still a third run. The second solid catalyst was used to contact another reaction mixture which contained 10 ml chlorobenzene, 0.2 ml methylaluminum sesquichloride, and 5 ml pentene-1. After 1 hour and 20 minutes at room temperature, the reaction mixture was hydrolyzed and analyzed showing:

| Olefins | Weight % |
|---|---|
| pentenes | 69.6 |
| hexenes | 1.1 |
| heptenes | 1.6 |
| octenes | 27.7 |

This example shows that the NOCl treated solid $MoO_3Al_2O_3$/MASC catalyst system can be recovered and utilized in subsequent conversions with or without additional contact with MASC.

EXAMPLE III

Conversion of pentene-1 over $MoO_3$—$Al_2O_3$/EADC

A suspension of 5.5 g of a $MoO_3$—$Al_2O_3$ catalyst (extrudates previously heated at 1000°F for 5 hours) in 20 ml of chlorobenzene and 10 ml of pentene-1 was mixed with 0.5 ml of ethylaluminum dichloride (EADC). The mixture was stirred in a closed vessel at room temperature for 2 hours and then hydrolyzed. Analysis of the liquid phase of the reaction mixture (ethylene, propylene, and butenes were also present in the gas phase) showed the following results:

| Olefins | Weight % |
|---|---|
| pentenes | 84.3 |
| hexenes | 4.8 |
| heptenes | 5.4 |
| octenes | 5.5 |

This examples shows that an alumina-supported molybdenum oxideethylaluminum dichloride catalyst system is active for olefin conversion at room temperature.

EXAMPLE IV

Conversion of pentene-1 over NO-treated $MoO_3$—$Al_2O_3$/MASC

A suspension of 12 g of a $MoO_3$—$Al_2O_3$ catalyst (which contained about 13 weight per cent $MoO_3$ and which had been activated by calcination at elevated temperatures) in 20 ml of chlorobenzene was treated with NO at 25 psig for about 16 hours at room temperature. A 10 ml quantity of pentene-1 was then added together with 0.5 ml of methylaluminum sesquichloride. This reaction was then allowed to proceed with stirring and the ethylene product was allowed to vent. A sample was taken after 30 minutes and the system was closed at that time. Several additional samples were taken at intervals. The analysis of the liquid phase of these samples showed the following results in weight per cent.

| Olefin | 0.5 hr | 2.5 hr | 8 hr | 26 hr |
|---|---|---|---|---|
| Ethylene | trace | trace | trace | trace |
| Propylene | trace | trace | 1.2 | trace |
| Butenes | trace | trace | 6.7 | 5.5 |
| Pentenes | 52.3 | 34.5 | 21.9 | 9.7 |
| Hexenes | 2.4 | 7.0 | 21.7 | 27.7 |
| Heptenes | 3.0 | 6.9 | 17.2 | 21.9 |
| Octenes | 42.2 | 51.7 | 31.2 | 31.7 |

There appeared to be little, if any, polymer formation.

This example shows a nitric oxide-treated solid $MoO_3$—$Al_2O_3$ is also effective for the conversion of olefins at room temperature when in the presence of a suitable organoaluminum halide such as MASC. The effect of the reaction time on the product distribution is also shown.

EXAMPLE V

Conversion of octene-1 over NO-treated $MoO_3$—$Al_2O_3$/MASC

Using the same activated molybdena-alumina catalyst described in Example III and the same general procedure described in Example III, 12 g of the solid catalyst was treated with NO at 20 psig for 2 hours. The NO was vented, 20 ml of octene-1 was added followed by 0.5 ml of methylaluminum sesquichloride. This reaction mixture was stirred at room temperature while allowing the ethylene product to vent. After stirring for 30 minutes, a sample of the liquid phase of the reaction mixture was withdrawn and the system was closed. Another sample was taken after a 3-hour reaction period. Analysis of these samples showed the following results in weight per cent:

| Olefin | | 0.5 hr | 3 hr |
|---|---|---|---|
| $C_7$ | | 1.0 | 2.2 |
| $C_8$ | | 70.4 | 54.3 |
| $C_9$ | | 0.4 | 2.0 |
| $C_{10}$ | | 0.2 | 0.9 |
| $C_{11}$ | | trace | trace |
| $C_{12}$ | | trace | 0.2 |
| $C_{13}$ | | 0.5 | 2.4 |
| $C_{14}$ | | 25.4 | 34.0 |
| $C_8$ | dimers | 1.6 | 3.8 |

The presence of ethylene, propylene, butenes, and hexenes could also be detected in the reaction mixture but are not shown in the above table.

This example shows that octane-1 0 can also be converted utilizing the NO treated $MoO_3$—$Al_2O_3$/MASC catalyst system of the present invention.

EXAMPLE VI

Conversion of pentene-1 over $WO_3$—$SiO_2$/MASC

A reaction mixture was prepared which contained 4.5 g of a $WO_3$—$SiO_2$ solid olefin conversion catalyst (which contained 6.8 weight percent $WO_3$ and which had been activated by calcination at elevated temperatures), 10 ml chlorobenzene, 10 ml pentene-1, and 0.5 ml methylaluminum sesquichloride.

After a 4.5 hour reaction period at room temperature, analysis of the liquid phase of the reaction mixture showed the presence of 80.2 weight percent pentenes, 13.1 weight percent hexenes, and 6.8 weight percent heptenes. Ethylene and other lower olefins were also present in the gas phase of the reaction mixture.

This example demonstrates that the silica-supported tungsten oxide when combined with a suitable organoaluminum halide such as MASC can be used to convert olefins at low temperatures.

EXAMPLE VII

Conversion of pentene-1 over NO-treated $WO_3$—$SiO_2$/MASC

The run of Example VI was repeated except a 3.5 g quantity of the $WO_3$—$SiO_2$ catalyst was treated with NO for 2 hours at 25 psig and utilized in place of the untreated $WO_3$—$SiO_2$. The analysis of the liquid phase of the reaction mixture showed the presence of, after a 0.5 hour reaction period, 84.9 weight percent pentenes, 1.3 weight percent hexenes, 4.2 weight percent heptenes, and 9.6 weight percent octenes.

This example shows that the nitric oxide treatment of the solid $WO_3$—$SiO_2$ increases the activity of the catalyst system which employs the silica-supported tungsten oxide solid catalyst.

EXAMPLE VIII

Conversion of propylene over NO-treated $MoO_3$—$Al_2O_3$/MASC

A reaction mixture was prepared containing 7.0 g of an activated $MoO_3$—$Al_2O_3$ (similar to the NO-treated solid catalysts of earlier examples), 20 0 ml chlorobenzene, 1 ml. methylaluminum sesquichloride, and 65 g propylene in an autoclave. The reaction was allowed to proceed for about 3 hours at room temperature.

A sample of the vapor phase of the reaction mixture, taken after about a 3-hour reaction period, showed the presence of 2.1 weight percent ethylene, 87.4 0 weight percent propylene, and 10.4 weight percent butenes.

This example shows that propylene an also be converted by the catalyst system of the present invention.

EXAMPLE IX

Conversion of pentene-1 over NO-treated $MoO_3$—$Al_2O_3$/DEAC or EASC

Run 1

A reaction mixture was prepared which contained 10 g of a $MoO_3$—$Al_2O_3$ solid catalyst (similar to the NO-treated catalysts described earlier), 10 ml of chlorobenzene, 10 ml of pentene-1, and 0.5 ml of diethylaluminum chloride (DEAC). The reaction mixture was stirred for ½ hour at room temperature at which time the liquid phase was sampled and analyzed with the following results. The analysis showed the presence of 80.8 weight percent pentenes, 0.3 weight percent hexenes, 2.2 weight percent heptenes, and 16.8 weight percent octenes. Other lower olefins were also present within the reaction zone.

This run shows that diethylaluminum chloride is effective in combination with NO treated $MoO_3$—$Al_2O_3$ to provide an active catalyst system of the present invention.

Run 2

In another run essentially identical with that described above, ethylaluminum sesquichloride (EASC) was used as the organoaluminum halide and the analysis of the liquid phase, after 1 hour, showed the presence of 72.2 weight percent pentenes, 4.5 weight percent hexenes, 7.4 weight percent heptenes, and 16.0 weight percent octenes. This illustrated that ethylaluminum sesquichloride is also effective when combined with NO treated $MoO_3$—$Al_2O_3$ in providing the catalyst system of this invention.

EXAMPLE X

Conversion of pentene-1 over NO-treated $WO_3$—$SiO_2$/EADC

A reaction mixture was prepared which consisted of 3.5 g of a $WO_3$—$SiO_2$ solid catalyst (containing 6.8 weight per cent $WO_3$, which had been activated in flowing air at 1000°F, and which had been treated with NO at 25 psig for 2 hours), 10 ml chlorobenzene, 10 ml pentene-1, 0 and 0.5 ml. of ethylaluminum dichloride (EADC). After 30 minutes reaction at room temperature, analysis of the liquid phase of the reaction mixture showed the presence of 33.1 weight percent pentenes, 28.2 weight percent hexenes, 19.8 weight percent heptenes, and 18.8 weight percent octenes.

This run shows that NO-treated $Wo_3$—$SiO_2$/EADC is very effective in converting olefins such as pentene-1.

EXAMPLE XI

Conversion of octene-1 over NO-treated $MoO_3$—$Al_2O_3$/MASC in a refluxing system A 12 g quantity of the $MoO_3$—$Al_2O_3$ catalyst which had been activated by calcination and treated with NO, was suspended in 25 ml cyclohexane and treated with MASC. After 20 minutes, the organic layer was decanted and the solid catalyst was washed with two 20-ml portions of cyclohexane. The resultant solid material was then dried under reduced pressure.

While under a nitrogen atmosphere, the above-treated solid catalyst was transferred to a distillation column making a bed 14 mm by about 14 cm. A distillation pot, containing 30 ml of octene-1, was placed under the packed column and heated for 30 minutes. During this period, the pot temperature rose up to 174°C and the head temperature rose up to 79°C. The system was operated so that the contents of the pot were allowed to vaporize and contact the catalyst bed and then reflux back into the pot. The light olefin products which were formed were allowed to escape through the top of the column. During the run, the temperature in the reaction zone was in the range of from about 75 to about 150°C.

Analysis of the liquid phase of the reaction mixture showed the following:

| Olefin | Weight % |
|---|---|
| $C_7$ | 1.5 |
| $C_8$ | 14.3 |
| $C_9$ | 9.9 |
| $C_{10}$ | 4.0 |
| $C_{11}$ | 4.5 |
| $C_{12}$ | 9.4 |
| $C_{13}$ | 18.7 |
| $C_{14}$ | 25.7 |
| $C_{15-16}$ | 12.0 |

This run shows that the catalyst system of the present invention is effective for the conversion of olefins at temperatures encountered in a refluxing system, i.e., between 75° to about 150°C.

EXAMPLE XII

Conversion of pentene-2 over $MoO_3$—$CoO$—$Al_2O_3$/MASC

A reaction mixture containing 20 ml pentene-2, 8 g of a 28–48 mesh alumina-supported cobalt molybdate catalyst, and a quantity of MASC equivalent to 0.75 weight percent of the solid catalyst component was prepared. The solid catalyst contained about 11.0 weight percent $MoO_3$ and about 3.4 weight percent CoO and was base-treated with about 1 weight percent KOH by aqueous impregnation. The solid catalyst was activated, following the impregnation with KOH but prior to contact with MASC, by heating in air for 24 hours at 1050°F and then flushed with nitrogen.

The reaction was stirred for 4 hours at room temperature. At 0.5 hour, the conversion was 35.2 percent and the selectivity to $C_4$ and $C_6$ olefins was 99.1 percent. After 4 hours, the conversion was 52.4 percent and the selectivity was 97.6 percent.

This example demonstrates that the alumina-supported cobalt molybdate/MASC catalyst system is effective in converting olefins such as pentene-2.

EXAMPLE XIII

Conversion of pentene-2 over $MoO_3$—$Al_2O_3$ /MASC

In a manner similar to that of the preceding examples, a reaction mixture containing 20 ml pentene-2, 8 g of a $MoO_3$—$Al_2O_3$ (13% $MoO_3$) catalyst, and a quantity of MASC equivalent to 0.75 weight percent based on the weight of the solid catalyst component was prepared. The solid catalyst component was treated with 1.0 weight percent KOH and was activated for 20 minutes at 1050°F in air.

The reaction mixture was stirred for 2 hours at room temperature. Periodic sampling and analysis of the reaction mixture showed the following results.

| Time, hr | 0.5 | 1 | 2 |
|---|---|---|---|
| Conversion, per cent | 47.3 | 50.6 | 50.7 |
| Analysis, weight per cent | | | |
| $C_3$ olefin | 0.01 | 0.02 | 0.02 |
| $C_4$ olefin | 18.16 | 21.10 | 19.67 |
| $C_5$ olefin | 52.74 | 49.38 | 49.24 |
| $C_6$ olefin | 28.97 | 29.43 | 30.86 |
| $C_7$ olefin | 0.06 | 0.07 | 0.11 |
| $C_{8+}$ olefin | 0.05 | nil | 0.10 |
| Selectivity to $C_4$ and | | | |
| $C_6$, per cent | 99.7 | 99.8 | 99.5 |

This run demonstrates the high conversions and the high selectivity capable of the process of the present invention.

EXAMPLE XIV

Effect of base treatment on $MoO_3$—$Al_2O_3$/MASC system

Several runs were made in which pentene-2-was converted with the $MoO_3$—$Al_2O_3$/MASC catalyst system and wherein the solid portion of the catalyst was base-treated with varying amounts of KOH. The catalysts were activated 24 hours in air and the conversion was carried out at room temperature using 8 g of the catalyst and 20 ml pentene-2. Sufficient MASC was present to total 0.75 weight percent of the solid catalyst.

Sampling and analysis after 1 hour reaction time showed the following results.

| % KOH | 0 | 0.5 | 1.0 | 1.5 |
|---|---|---|---|---|
| % Conversion | 50.8 | 33.9 | 15.9 | 2.1 |
| % Selectivity | 93.7 | 98.8 | 98.6 | 98.6 |

These results show that the base treatment improves the selectivity of the reaction.

EXAMPLE XV

Effect of MASC quantity on $MoO_3$—$Al_2O_3$/MASC System

A series of runs were carried out to show the effect of MASC concentration of the $MoO_3$—$Al_2O_3$/MASC catalyst system. In each run, the solid catalyst was treated with 1.5 weight percent KOH and activated about 16 hours in air. A 20 ml quantity of pentene-2 and 8 g of solid catalyst were used in each run carried out at room temperature. The quantity of MASC (applied to the solid catalyst in chloroform solution followed by evaporation of the solvent) was varied.

Sampling and analysis of the reaction mixture after 1 hour reaction time showed the following.

| % MASC | 0 | 0.5 | 0.75 | 1.5 | 6.1 |
|---|---|---|---|---|---|
| (Al:Mo ratio) | | (0.03) | (0.04) | (0.08) | (0.3) |
| % Conversion | 3.0 | 1.5 | 42.7 | 38.4 | 43.2 |
| % Selectivity | 100 | 91 | 99 | 99 | 94 |

These data show that the $MoO_3$—$Al_2O_3$/MASC catalyst is effective in converting olefins in accordance with the olefin reaction by the process of this invention when the amount of MASC of the catalyst system is varied.

EXAMPLE XVI

Conversion of pentene-2 over $WO_3$—$SiO_2$/MASC

A 25 ml quantity of pentene-2 was converted in a 2 hour run in the presence of 8 g of a 28–48 mesh $WO_3$—$SiO_2$ (6.8% WO) catalyst which was activated at 1050°F for 20 minutes in air. The catalyst was treated with 0.75 weight percent MASC. The conversion was carried out at room temperature in a stirred reactor.

Periodic sampling and analysis showed the following results.

| Time, hr | 0.5 | 1.0 | 2.0 |
|---|---|---|---|
| Conversion, per cent | 32.8 | 45.5 | 52.5 |
| Analysis, weight per cent | | | |
| $C_3$ olefin | 0.03 | 0.05 | 0.11 |
| $C_4$ olefin | 12.71 | 17.43 | 21.03 |
| $C_5$ olefin | 67.17 | 54.18 | 47.75 |
| $C_6$ olefin | 18.01 | 24.56 | 26.17 |
| $C_7$ olefin | 0.17 | 0.37 | 0.89 |
| $C_{8+}$ olefin | 1.91 | 3.10 | 4.34 |
| Selectivity to C and $C_6$, per cent | 93.6 | 92.3 | 89.8 |

These data show that the $WO_3$—$SiO_2$/MASC catalyst system is capable of good conversion and selectivity.

EXAMPLE XVII

Ethylene Cleavage of Cyclooctene

A mixture of cyclooctene and ethylene was converted at room temperature and at 15 psig pressure in a 2.5 hour batch reaction. A 20 ml quantity of the cyclooctene was contacted with 8 g of the $MoO_3/Al_2O_3$ catalyst which had been treated with 1 percent KOH and 1 percent methylaluminum sesquichloride as in previous examples. The batch reactor was maintained at 15 psig by ethylene pressure.

At the conclusion of the reaction the reaction mixture was analyzed and the analysis showed that 8 percent of the cyclooctene had been converted and the selectivity to the cleaved product, 1,9-decadiene was about 63 percent.

EXAMPLE XVIII

Conversion of Cyclopentene over Triisobutylaluminum-Treated $MoO_3/Al_2O_3$

Cyclopentene was converted to a rubbery polymer by contacting about 15 g of cyclopentene with about 8 g of the $MoO_3/Al_2O_3$ catalyst which had been treated with about 1 percent KOH and about 1 percent by weight of triisobutylaluminum based on the weight of the catalyst. The treatment was carried out as in previous examples. The reaction mixture began to thicken almost instantly and about 32 ml of cyclohexane was added to facilitate stirring. The reaction was continued for about 5 hr. at room temperature and at atmospheric pressure. About 5 g of a rubbery polymeric product was recovered.

Reasonable variations and modifications are possible without departing from the spirit and scope of the invention.

I claim:

1. As a composition of matter, a catalyst consisting essentially of an admixture of a composite of (a) molybdenum oxide or tungsten oxide associated with a suitable support material, said composite having been activated in flowing air at a temperature of from about 500°F to about 1600°F, and (b) at least one organoaluminum compound of the formula $R_aAlX_b$ wherein R is a saturated aliphatic or aromatic hydrocarbon having up to 20 carbon atoms; X is chlorine, bromine, iodine or fluorine, a is an integer of at least 1; b is 0, 1 or 2; and the total of a and b is 3, wherein the (a) component of the catalyst is contacted with excess nitric oxide or nitrosyl halide, or with a sufficient amount of an alkali or alkaline earth metal hydroxide or carbonate to provide from about 0.005 to about 5 weight percent of said alkali or alkaline earth metal hydroxide or carbonate prior to contact with (b) and subsequent to being subjected to high temperature; and wherein the molar ratio of (b) to (a) is in the range of from about 0.005:1 to 20:1 mols of (b) per mol of molybdenum or tungsten oxide present in (a).

2. A composition of matter in accordance with claim 1 wherein the support material for the (a) component of the catalyst is alumina, silica, silica-alumina, magnesia-titania, thoria, aluminum phosphate, zirconium phosphate, titanium phosphate, calcium phosphate, magnesium phosphate, or mixtures thereof.

3. A composition of matter according to claim 1 wherein the (a) component of the catalyst system is molybdenum oxide supported on alumina, or tungsten oxide supported on silica.

4. A composition of matter according to claim 1 wherein the organoaluminum compound is ethylaluminum dichloride, diethylaluminum chloride, ethylaluminum sesquichloride, methylaluminum sesquichloride, or triisobutylaluminum.

5. The composition of claim 1 wherein the (a) component of the catalyst is contacted with said nitric oxide or said nitrosyl halide.

6. The composition of claim 1 wherein the molar ratio of (b) to (a) is in the range of from about 0.01:1 to about 10:1 mols of (b) per mol of the molybdenum or tungsten oxide contained in (a).

7. A composition of matter according to claim 1 wherein the (a) component comprises molybdenum oxide supported on alumina or tungsten oxide supported on silica which has been contacted with nitrosyl chloride and then admixed with the (b) component comprising ethylaluminum sesquichloride.

8. A composition of matter according to claim 1 wherein the (a) component comprises molybdenum oxide supported on alumina or tungsten oxide supported on silica which has been contacted with nitric oxide and subsequently admixed with the (b) component comprising methylaluminum sesquichloride, diethylaluminum chloride, or ethylaluminum sesquichloride.

9. A composition of matter according to claim 1 wherein the (a) component of the catalyst is molybdenum oxide supported on alumina which has been contacted with potassium hydroxide and then admixed with methylaluminum sesquichloride or triisobutylaluminum.

10. The composition of matter according to claim 1 wherein the (a) component of the catalyst is contacted with an alkali metal hydroxide which is potassium hydroxide.

11. As a composition of matter, a catalyst consisting essentially of an admixture of (a) a composite of molybdenum oxide or tungsten oxide associated with a suitable support material, said composite having been activated in flowing air at a temperature of from about 500°F to about 1600°F, and (b) at least one organoaluminum halide compound having the formula $R_aAlX_b$ wherein R is a saturated aliphatic or aromatic hydrocarbon having up to 20 carbon atoms; X is chlorine, bromine, iodine, or fluorine; a is 1 or 2; b is 1 or 2; and the total of a and b is 3; and wherein the molar ratio of (b) to (a) is in the range of from about 0.005:1 to about 20:1 mols of (b) per mol of molybdenum or tungsten oxide contained in (a).

12. A composition of matter according to claim 11 wherein the suitable support material for the (a) component of the catalyst is alumina, silica, silica-alumina, magnesia-titania, thoria, aluminum phosphate, zirconium phosphate, titanium phosphate, calcium phosphate, magnesium phosphate, or mixtures thereof.

13. The composition of claim 11 wherein the molar ratio of (b) to (a) is in the range of from about 0.01:1 to about 10:1 mols of (b) per mol of the molybdenum or tungsten oxide contained in (a).

14. A composition of matter according to claim 11 wherein the (a) component of the catalyst system is molybdenum oxide supported on alumina, or tungsten oxide supported on silica.

15. A composition of matter according to claim 11 wherein the organoaluminum halide compound is ethylaluminum dichloride, diethylaluminum chloride, ethylaluminum sesquichloride, or methylaluminum sesquichloride.

16. A composition of matter according to claim 11 wherein the (a) component of the catalyst is molybdenum oxide supported on alumina or tungsten oxide supported on silica which is admixed with methylaluminum sesquichloride or ethylaluminum dichloride.

* * * * *